(12) United States Patent
Engelhardt et al.

(10) Patent No.: US 6,785,302 B1
(45) Date of Patent: Aug. 31, 2004

(54) OPTICAL SYSTEM IN THE RAY PATH OF A CONFOCAL FLUORESCENCE MICROSCOPE

(75) Inventors: Johann Engelhardt, Bad Schoenborn (DE); Heinrich Ulrich, Heidelberg (DE); William C. Hay, Hoppenheim (DE)

(73) Assignee: Leica Microsystems Heidelberg GmbH, Heidelberg (DE)

( * ) Notice: Subject to any disclaimer, the term of this patent is extended or adjusted under 35 U.S.C. 154(b) by 0 days.

(21) Appl. No.: 09/554,083

(22) PCT Filed: Sep. 13, 1999

(86) PCT No.: PCT/DE99/02910

§ 371 (c)(1),
(2), (4) Date: May 12, 2000

(87) PCT Pub. No.: WO00/16149

PCT Pub. Date: Mar. 23, 2000

(30)  Foreign Application Priority Data

Sep. 15, 1998 (DE) .......................................... 198 42 153

(51) Int. Cl.⁷ .......................... H01S 3/121; G02B 21/00
(52) U.S. Cl. ............................. 372/15; 372/98; 372/99; 372/107; 378/44; 356/318; 359/368; 359/387
(58) Field of Search .............................. 372/15, 98, 99, 372/107; 378/44

(56)  References Cited

U.S. PATENT DOCUMENTS

| | | | |
|---|---|---|---|
| 4,744,663 A | | 5/1988 | Hamashima et al. ......... 356/375 |
| 5,127,730 A | * | 7/1992 | Brelje et al. ................. 356/318 |
| 5,210,765 A | | 5/1993 | Flint et al. ..................... 372/23 |
| H1344 H | * | 8/1994 | Baldauf et al. ................ 435/20 |
| 5,428,441 A | * | 6/1995 | Ogino et al. ................... 356/73 |
| 5,703,714 A | * | 12/1997 | Kojima ........................ 359/368 |
| 5,734,498 A | * | 3/1998 | Krasieva et al. ............ 359/387 |
| 6,111,259 A | * | 8/2000 | Arai ......................... 250/459.1 |
| 6,445,491 B2 | * | 9/2002 | Sucha et al. ................. 359/330 |

FOREIGN PATENT DOCUMENTS

| | | |
|---|---|---|
| EP | 0 801 301 | 4/1997 |
| JP | 3-269405 | 12/1991 |
| JP | 10-96862 | 4/1998 |

\* cited by examiner

*Primary Examiner*—Paul Ip
*Assistant Examiner*—Cornelius H. Jackson
(74) *Attorney, Agent, or Firm*—Foley & Lardner LLP

(57)  ABSTRACT

The invention relates to an optical system in the ray path of a confocal fluorescence microscope, comprising at least one laser light source (1, 2), a device positioned in the illuminating/detecting beam (3, 4, 5) for separating the exciting light (8) from the fluorescent light (9), an objective (10) arranged between the device and the object (7), and a detector (11) positioned downstream of the device situated in the detecting beam (5). The aim of the invention is to increase the fluorescence yield of the system while retaining its compact structure. To this end the separating device comprises a mirror (13) which is dimensioned and positioned in the illuminating and/or detecting beam (3, 4, 5) in such a way that for the dark-field illumination of the object (7) it reflects the non-expanded exciting beam arriving from the laser light source (1, 2) into the objective (10) and permits the transit of the fluorescence light (9) arriving from the object (7) in the direction of the detector (11) with full numerical aperture, the fluorescent light beam being reduced by the mirror (13) cross-section active in the detecting beam (5).

15 Claims, 2 Drawing Sheets

OPTICAL SYSTEM IN THE RAY PATH OF A CONFOCAL FLUORESCENCE MICROSCOPE

BACKGROUND OF THE INVENTION

The invention relates to an optical arrangement in the beam path of a confocal fluorescence microscope, having at least one laser light source, a device arranged in the illumination/detection beam path to separate the exciting light reflected at the object from the fluorescent light radiated by the object, an objective arranged between the device and the object, and a detector arranged downstream of the device in the detection beam path.

In practice, it has already been known for years to use a dichroic beam splitter to separate the exciting light reflected at the object from the fluorescent light radiated by the object. In the simultaneous multicolor application, a number of dichroic beam splitters are correspondingly used. The fluorescent light freed of the reflected exciting light is detected by means of a special detector—after being separated by means of beam splitters. The beam splitters used in practice are generally expensive. Furthermore, these beam splitters are only little suited to quantitative comparative measurements at high precision and with high measurement dynamics, especially since these beam splitters are, inter alia, also temperature-dependent. Furthermore, dichroic beam splitters have transmission losses of about 10% for the detection.

If one were to use, for example, a beam splitter that was independent of wavelengths, this would doubtless reduce the costs. However, the disadvantage in this case would be that it would be necessary to filter out the scattered light from the exciting light before detection, for example by using a blocking filter. This is again complicated from a constructional point of view and once again gives rise to costs. In addition, the result is that the fluorescence yield is reduced. However, simultaneous multicolor applications are then not possible.

If a simple beam splitter is used, in addition reflected scattered light from the exciting light gets back into the laser light source and interferes with the stimulated emission taking place there, which in turn makes itself noticeable through undesired intensity fluctuations in the laser light.

For the highest resolution applications the same numerical aperture is used for the illumination and for scanning. This leads to an illumination focus which is very small in the lateral direction, so that relatively long recording times are necessary. For applications in which the resolution plays a subordinate role, this procedure is disadvantageous because of the longer recording times.

With regard to confocal fluorescence microscopy, reference is made, merely by way of example, to Engelhardt and Knebel in "Physik in unserer Zeit" [Physics in our time], Vol. 24, 1993, number 2 "Confocal laser scanning microscopy", and D. K. Hamilton and T. Wilson in Appl. Phys. B 27, 1982, 211–213 "Three-dimensional Surface Measurement Using the Confocal Scanning Microscope".

SUMMARY OF THE INVENTION

The present invention is, then, based on the object of configuring and developing an optical arrangement in the beam path of a confocal fluorescence microscope in such a way that it is possible to implement an increase in the fluorescence yield with a simple design by comparison with the generic arrangement with a conventional dichroic beam splitter.

The optical arrangement according to the invention in the beam path of a confocal fluorescence microscope achieves the above object by means of the features of patent claim 1. According to this claim, the optical arrangement mentioned at the beginning is characterized in that the device comprises a mirror, and in that the mirror is dimensioned and arranged in the illumination/detection beam path in such a way that, for dark-field illumination of the object, it reflects the non-widened exciting beam coming from the laser light source into the objective and permits the fluorescent light coming from the object to pass in the direction of the detector with full numerical aperture, reduced by the effective cross section of the mirror in the detection beam path.

According to the invention, it has firstly been found that the device comprises a mirror, and in that the mirror is dimensioned and arranged in the illumination/detection beam path in such a way that, for dark-field illumination of the object, it reflects the non-widened exciting beam coming from the laser light source into the objective and permits the fluorescent light coming from the object to pass in the direction of the detector with full numerical aperture, reduced by the effective cross section of the mirror in the detection beam path.

According to the invention, it has further been found that the device for separating the exciting light reflected at the object from the fluorescent light radiated by the object can be—instead of a conventional dichroic beam splitter—a mirror which is arranged in the illumination/detection beam path. In this case, this mirror is to be dimensioned in such a way—sufficiently small—that, for dark-field illumination of the object, it reflects the non-widened exciting beam coming from the laser light source into the object and permits the fluorescent light coming from the object to pass in the direction of the detector with full numerical aperture, the fluorescent light being reduced by the effective cross section of the mirror in the detection beam path. The main reflection of the exciting light reflected by the object is advantageously reflected out of the detection beam path at the mirror.

Because of the sufficiently small configuration of the mirror or of the reflective area, only the non-widened exciting beam is reflected into the objective. By illuminating with a "small" numerical aperture of this type (for example 10% of the otherwise usual aperture), "dark-field illumination" is achieved which exhibits an elongated focal range with a well-defined focal diameter along the optical axis. According to the invention, an adequate illumination tolerance in the object position along the optical axis is achieved, which has a particularly beneficial effect on specific applications in confocal fluorescence microscopy. Furthermore, illumination with high intra-scene dynamics is ensured. The advantage of such high intra-scene dynamics is that, for example, two immediately adjacent objects with different absolute fluorescent intensities, for example object A at 100% and object B at 0.05%, can be measured separately from each other in the same confocal plane without "over-illuminating" the lighter object.

In a particularly advantageous way, the mirror is dimensioned and configured to be small in such a way that, for the fluorescent light to be detected, it causes a loss in the detection beam path of about 1%. This permits efficient detection with a particularly high dynamic range.

Within the context of a particularly simple embodiment, the mirror used here could be designed as an independent component, the mirror in turn being carried by a holder. Within the context of such a configuration, the use of a conventional beam splitter is completely dispensed with, since here only the small mirror is specifically arranged at an appropriate point in the beam path. Within the context of a further alternative, the mirror could be designed as a preferably integrally silvered area of an—otherwise conventional—beam splitter, the mirror or the silvered area being arranged or formed at least largely at the center of the beam splitter. This small—integral—mirror could be approximately circular or elliptical or oval. Ultimately, what is concerned here is a silvered area at the center of a beam splitter which, just like an isolated mirror, reflects the non-widened exciting beam into the objective. Here, too, illumination takes place with an extremely small numerical aperture, to the benefit of the dynamics.

The non-reflective area of the beam splitter could exhibit approximately 10% reflection and 90% transmission in the direction of the detector. In concrete terms, this could be an anti-reflection (AR) coating on that side of the beam splitter facing the detector. This beam splitter permits the fluorescent light to pass in the direction of the detector in accordance with the conventional—infinite—beam path at full numerical aperture—reduced by the fluorescent light incident on the silvered area. The silvered area produces an extremely low loss for the fluorescent light to be detected, specifically depending on the size of the mirror. Here, it is possible to realize losses of only 1%, which leads to the high dynamics already previously mentioned.

Moreover, the non-reflective area of the beam splitter could be configured and, if appropriate, coated in such a way that the optical properties of the non-reflective area of the beam splitter are at least largely independent of temperature. This is to the benefit of the reproducibility of the measurement.

Now, it is not only fluorescent light which passes from the object into the detection beam path, but also back-reflection of the exciting light. Such back-reflection is undesired. In order to suppress the back-reflection of the exciting light at the object back into the laser light source, the object could be arranged crookedly. This means that the object itself is not arranged orthogonal to the optical axis, so that the result for the back-reflected exciting light is a separate beam path which is offset at least slightly—physically—with respect to the illumination beam path. It is readily possible to arrange conventional light traps in this special beam path, specifically in order to mask out the back-reflected exciting light effectively.

In the event of a desired object displacement, for example in order to find a further object, it is of particular advantage if the object can be moved in its plane in such a way that the illuminated object area is always at the same distance from the objective. As a result, the light reflected and/or scattered at the object according to the above embodiments is not reflected back into the laser light source but into a light trap via the special beam path.

As an alternative to the precaution of a light trap, the mirror—within the context of a configuration as an isolated component—could have an absorbing area to absorb the exciting light scattered and/or reflected by the object. In this case, the precaution of special light traps is no longer necessary, which results in a reduction in the physical size of the arrangement. Thus, the mirror—within the context of a circular or elliptical or oval configuration—could have a reflective area and an absorbing area.

It is likewise possible for the beam splitter, apart from the silvered area, to have an absorbing area to absorb the exciting light scattered and/or reflected by the object. Within the context of such a configuration, the precaution of a special light trap can also be dispensed with, so that this configuration also involves the advantage of being able to construct the arrangement with the smallest space requirement.

Finally, it is of quite particular advantage if, by means of a suitable ratio between beam divergence and wavelength of the laser light sources used, an at least approximately identical—axial—focal position is possible. As a result, on the one hand the necessary illumination tolerance in the object position along the optical axis is provided and, on the other hand, illumination with high intra-scene dynamics is ensured. For this purpose, reference is made to the above embodiments to avoid repetition.

There are then various possibilities of configuring and developing the teaching of the present invention in an advantageous way. For this purpose, reference should be made to the following explanation of exemplary embodiments of the invention, using the drawing. In connection with the explanation of the preferred exemplary embodiments of the invention using the drawing, configurations and developments of the teaching which are generally preferred will also be explained. In the drawing:

There are then various possibilities of configuring and developing the teaching of the present invention in an advantageous way. For this purpose, reference should be made on the one hand to the claims subordinate to patent claim 1 and on the other hand to the following explanation of exemplary embodiments of the invention, using the drawing. In connection with the explanation of the preferred exemplary embodiments of the invention using the drawing, configurations and developments of the teaching which are generally preferred will also be explained. In the drawing

DETAILED DESCRIPTION OF THE EXEMPLARY EMBODIMENTS

Figure 1:
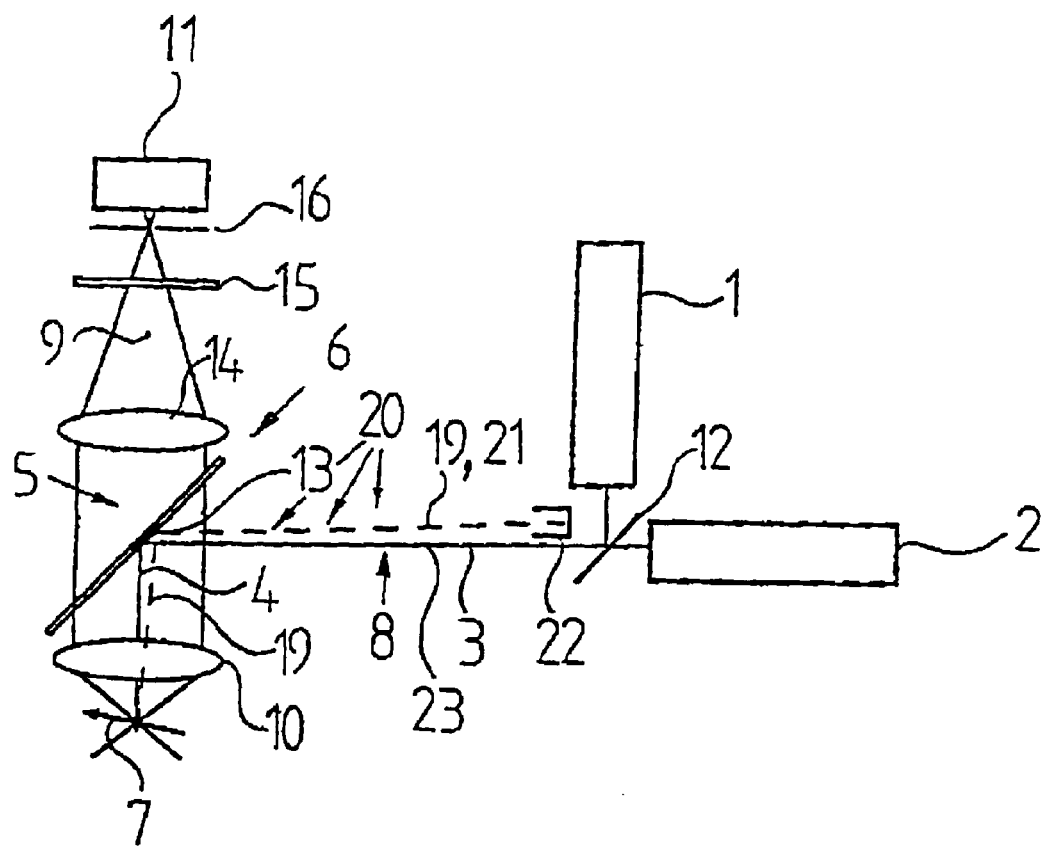
FIG. 1 shows, in a schematic illustration, the fundamental construction of an optical arrangement according to the invention in the beam path of a confocal fluorescence microscope.

FIG. 1 shows a schematic illustration of an exemplary embodiment of an optical arrangement in the beam path of a confocal fluorescence microscope, this arrangement—in the exemplary embodiment chosen here—comprising two laser light sources 1, 2, a device 6 arranged in the illumination/detection beam path 3, 4, 5 to separate the exciting light 8 reflected at the object 7 from the fluorescent light 9 radiated by the object 7, an objective 10 arranged between the device 6 and the object 7, and a detector 11 arranged downstream of the device 6 in the detection beam path 5.

It can be seen schematically from FIG. 1 that the exiting light 8 passes via a beam combiner 12 to the device 6, is reflected from the latter into the objective 10 and from there passes to the objet 7. The fluorescent light 9 in turn passes through the objective 10 to the device 6, passes through this, with the exception of the reflecting area formed in the manner according to the invention as a mirror 13, and passes via a tubular lens 14, a blocking-filter wheel 15 and a detection aperture 16 to the detector 11.

According to the invention, the device 6 comprises a mirror 13, the mirror 13 being dimensioned and arranged in the illumination/detection beam path 3, 4, 5 in such a way that, for dark-field illumination of the object 7, the non-widening exciting beam or the exciting light 8 coming from the laser light sources 1, 2 is reflected into the objective 10, and permits the fluorescent light 9 coming from the object 7 to pass in the direction of the detector 11 with full numerical aperture, reduced by the effective cross section of the mirror 13 in the detection beam path 4, 5.

Figure 2:
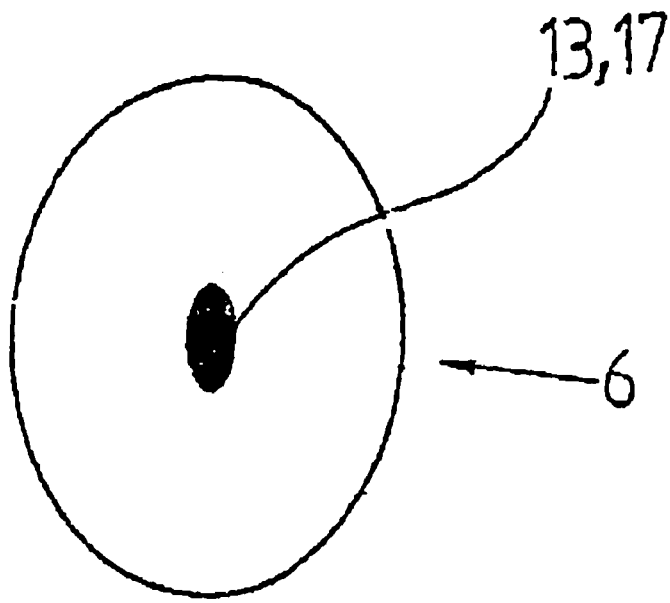
FIG. 2 shows, in a schematic illustration, a beam splitter with a central mirror.

In the exemplary embodiment shown in FIGS. 1 and 2, the device 6 is designed as a beam splitter, the mirror 13 being integrated centrally there.

Figure 3:
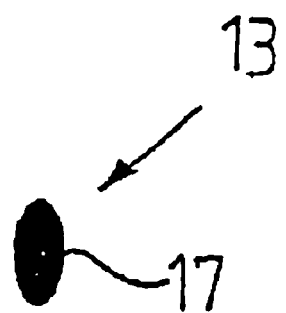
FIG. 3 shows, in a schematic illustration, a mirror which can be used instead of the beam splitter, as a separate component.

FIG. 3 shows an alternative configuration of the device 6, to the effect that this is purely and simply designed as a unique mirror 13, the mirror 13 being an independent component. The mirror 13 could have a totally silvered surface according to the illustration in FIG. 3.

Figure 4:
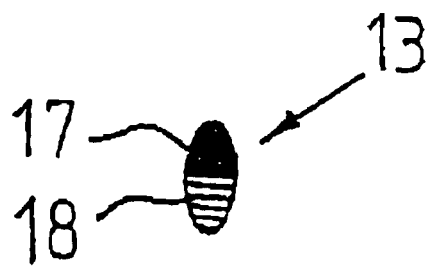
FIG. 4 shows, in a schematic illustration, a mirror with an integral reflecting and absorbing area.

In the exemplary embodiment illustrated in FIG. 4, the mirror 13 is likewise designed as a separate component, the surface of the mirror 13 being subdivided into a reflecting mirror surface 17 and into an absorbing surface 18. This measure renders the precaution of a separate light trap for any back-reflected exciting light 19 superfluous.

If, as the device 6, use is made of a beam splitter for example in accordance with the illustration in FIGS. 1 and 2, but also an embodiment according to FIGS. 3 and 4, the back-reflection or the back-reflected exciting light 19 can be made "nondamaging" by the sample or the object 7 being placed crookedly, that is to say not being arranged orthogonal to the optical axis 23. As a result, the back-reflected exciting light 19 is offset slightly from the illumination beam path 20 or the beam path of the exciting light 8, so that the back-reflected exciting light 19 is reflected back along its own beam path 21. Arranged at a suitable point there is a light trap 22 which, because of the alignment of the beam path 21, is located to the side of the illumination beam path 20 or the exciting light 8.

With regard to further advantageous configurations of the present invention, in order to avoid repetition, reference is made to the designs in the general part of the description.

List of Reference Symbols

1 Laser light source
2 Laser light source
3 Illumination beam path
4 Illumination/detection beam path
5 Detection beam path
6 Device for separating the exciting light reflected at the object from the fluorescent light radiated by the object
7 Object
8 Exciting light
9 Fluorescent light
10 Objective
11 Detector
12 Beam combiner
13 Mirror
14 Tubular lens
15 Blocking-filter wheel
16 Detection aperture
17 Mirror surface
18 Absorbing surface
19 Back-reflected exciting light
20 Illumination beam path
21 Beam path of the back-reflected exciting light
22 Light trap
23 Optical axis

What is claimed is:

1. An optical arrangement in a confocal fluorescence microscope, the confocal fluorescence microscope comprising:
    at least one laser light source that generates an exciting light in an illumination beam path;
    a detector arranged in a detection beam path;
    a device and an object arranged in the illumination beam path and the detection beam path, the device separating the exciting light reflected at the object from a fluorescent light radiated by the object, wherein the device comprises a beam splitter with a smaller centrally arranged mirror, wherein the mirror is centrally arranged with respect to a surface of the device on which the exciting light is incident;
    an objective arranged between the device and the object, and
    wherein said detector is arranged downstream of the device in the detection beam path, and wherein for dark-field illumination of the object, the mirror reflects a non-widened exciting beam coming from the at least one laser light source into the objective and permits the widened fluorescent light coming from the object to pass in the direction of the detector reduced by an effective cross section of the centrally arranged mirror on the beam splitter.

2. The arrangement according to claim 1, wherein the centrally arranged mirror on the beam splitter is dimensioned such that it causes a loss in the detection beam path of about one percent, such that the fluorescent light is detectable.

3. The arrangement according to claim 1, wherein the mirror is designed as an independent component, which is centrally arranged on the beam splitter.

4. The arrangement according to claim 3, wherein the mirror is carried by a holder.

5. The arrangement according to claim 1, wherein the mirror comprises an integrally silvered area of the beam splitter.

6. The arrangement according to claim 5, wherein the mirror is approximately circular.

7. The arrangement according to claim 5, wherein the mirror is approximately elliptical.

8. The arrangement according to claim 5, wherein a non-reflective area of the beam splitter exhibits approximately 10% reflection and 90% transmission in the direction of the detector.

9. The arrangement according to claim 5, wherein the optical properties of a non-reflective area of the beam splitter are substantially independent of temperature.

10. The arrangement according to claim 1, wherein the object is arranged in a non-orthogonal orientation with respect to an optical axis of the illumination beam path to suppress the exciting light reflected at the object from being reflected back into the at least one laser light source.

11. The arrangement according to claim 10, further comprising:
    a light trap disposed in a manner slightly offset with respect to the illumination beam path to trap back reflected exciting light.

12. The arrangement according to claim 1, wherein the object is movable in its plane so that the illuminated object area is always at the same distance from the objective.

13. The arrangement according to claim 1, wherein the mirror has an absorbing area to absorb the exciting light scattered by the object.

14. The arrangement according to claim 5, wherein in addition to the silvered area, the beam splitter has an absorbing area to absorb the exciting light scattered by the object.

15. The arrangement according to claim 1, wherein a ratio between beam divergence and a wavelength of the at least one laser light source used is selected so that at least an approximately identical focal position is implemented.

* * * * *